US009968435B2

(12) United States Patent
Saito et al.

(10) Patent No.: US 9,968,435 B2
(45) Date of Patent: May 15, 2018

(54) BODY LUMEN GRAFT BASE, PRODUCTION METHOD OF BODY LUMEN GRAFT BASE, AND BODY LUMEN GRAFT USING THE SAME

(71) Applicants: Terumo Kabushiki Kaisha, Tokyo (JP); TEIJIN LIMITED, Osaka-shi, Osaka (JP)

(72) Inventors: Aya Saito, Fujinomiya (JP); Kazuyoshi Tani, Fujinomiya (JP); Yoshikazu Takahashi, Fujinomiya (JP); Kengo Tanaka, Osaka (JP); Kumiko Tsuda, Tokyo (JP); Mie Kamiyama, Ibaraki (JP)

(73) Assignees: Terumo Kabushiki Kaisha, Tokyo (JP); TEIJIN LIMITED, Osaka (JP)

( * ) Notice: Subject to any disclaimer, the term of this patent is extended or adjusted under 35 U.S.C. 154(b) by 0 days. days.

(21) Appl. No.: 14/903,144

(22) PCT Filed: Jun. 23, 2014

(86) PCT No.: PCT/JP2014/066588
§ 371 (c)(1),
(2) Date: Jan. 6, 2016

(87) PCT Pub. No.: WO2015/005105
PCT Pub. Date: Jan. 15, 2015

(65) Prior Publication Data
US 2016/0135944 A1    May 19, 2016

(30) Foreign Application Priority Data

Jul. 10, 2013   (JP) ................................. 2013-144259

(51) Int. Cl.
*A61F 2/06*   (2013.01)
*A61F 2/07*   (2013.01)
(Continued)

(52) U.S. Cl.
CPC .................. *A61F 2/06* (2013.01); *A61F 2/07* (2013.01); *A61L 27/18* (2013.01); *A61L 27/507* (2013.01); *A61L 31/06* (2013.01)

(58) Field of Classification Search
CPC ................................... A61F 2/06; D03D 15/00
(Continued)

(56) References Cited

U.S. PATENT DOCUMENTS 4,743,250 A    5/1988 Kitagawa et al.
9,260,805 B2 *  2/2016 Fujita ..................... D04B 21/16
(Continued)

FOREIGN PATENT DOCUMENTS

EP           0179600 A2    4/1986
JP         2004-313310 A   11/2004
(Continued)

OTHER PUBLICATIONS

Communication dated Feb. 3, 2017, from the European Patent Office in counterpart European Application No. 14823314.1.
(Continued)

*Primary Examiner* — Suzette J Gherbi
(74) *Attorney, Agent, or Firm* — Sughrue Mion, PLLC

(57) ABSTRACT

The present invention provides a body lumen graft base that is a thin film, has adequate flexibility and low permeability, and can be inserted in a catheter with a small diameter. The body lumen graft base of the present invention is obtained by subjecting at least one surface of a woven fabric comprising a fiber having a total fineness of 1 to 80 decitex and a single fiber fineness of less than 0.1 decitex to press treatment using a calender machine.

13 Claims, 6 Drawing Sheets

(51) Int. Cl.
*A61L 31/06* (2006.01)
*A61L 27/18* (2006.01)
*A61L 27/50* (2006.01)

(58) Field of Classification Search
USPC .................................................. 623/1.5–1.54
See application file for complete search history.

(56) References Cited

U.S. PATENT DOCUMENTS

| | | | | |
|---|---|---|---|---|
| 9,347,157 | B2* | 5/2016 | Zhang | D04B 21/18 |
| 2003/0028239 | A1* | 2/2003 | Dong | A61F 2/07 |
| | | | | 623/1.13 |
| 2004/0162606 | A1* | 8/2004 | Thompson | A61F 2/06 |
| | | | | 623/1.22 |
| 2005/0085894 | A1* | 4/2005 | Kershner | A61F 2/07 |
| | | | | 623/1.13 |
| 2006/0009835 | A1* | 1/2006 | Osborne | A61F 2/06 |
| | | | | 623/1.13 |
| 2007/0098986 | A1* | 5/2007 | Goda | D01F 6/92 |
| | | | | 428/375 |
| 2009/0157164 | A1* | 6/2009 | McKinsey | A61F 2/07 |
| | | | | 623/1.13 |
| 2010/0268331 | A1 | 10/2010 | Simmelink et al. | |
| 2012/0184166 | A1* | 7/2012 | Kurihara | D01F 6/625 |
| | | | | 442/181 |
| 2012/0226344 | A1 | 9/2012 | Shirokaze et al. | |
| 2013/0041452 | A1* | 2/2013 | Fujita | D04B 21/16 |
| | | | | 623/1.13 |
| 2013/0053958 | A1* | 2/2013 | Macossay-Torres | A61F 2/08 |
| | | | | 623/13.2 |
| 2015/0352336 | A1* | 12/2015 | Kuppurathanam | A61M 25/10 |
| | | | | 606/194 |
| 2016/0320732 | A1* | 11/2016 | Tonomori | F16C 33/201 |
| 2016/0331510 | A1* | 11/2016 | Du | A61F 2/06 |

FOREIGN PATENT DOCUMENTS

| | | |
|---|---|---|
| JP | 2008-505713 A | 2/2008 |
| JP | 2011-229713 A | 11/2011 |
| JP | 2011-245283 A | 12/2011 |
| WO | 2006/014592 A1 | 2/2006 |
| WO | 2009077168 A2 | 6/2009 |

OTHER PUBLICATIONS

International Search Report for PCT/JP2014/066588 dated Sep. 30, 2014.
International Preliminary Report on Patentability issued from the International Bureau in counterpart International Application No. PCT/JP2014/066588, dated Jan. 21, 2016.
Communication dated Dec. 30, 2016 by the Chinese Patent Office in counterpart Chinese Patent Application No. 201480039277.3.
Communication dated Sep. 11, 2017 from the State Intellectual Property Office of the P.R.C. in counterpart Chinese application No. 201480039277.3.

* cited by examiner

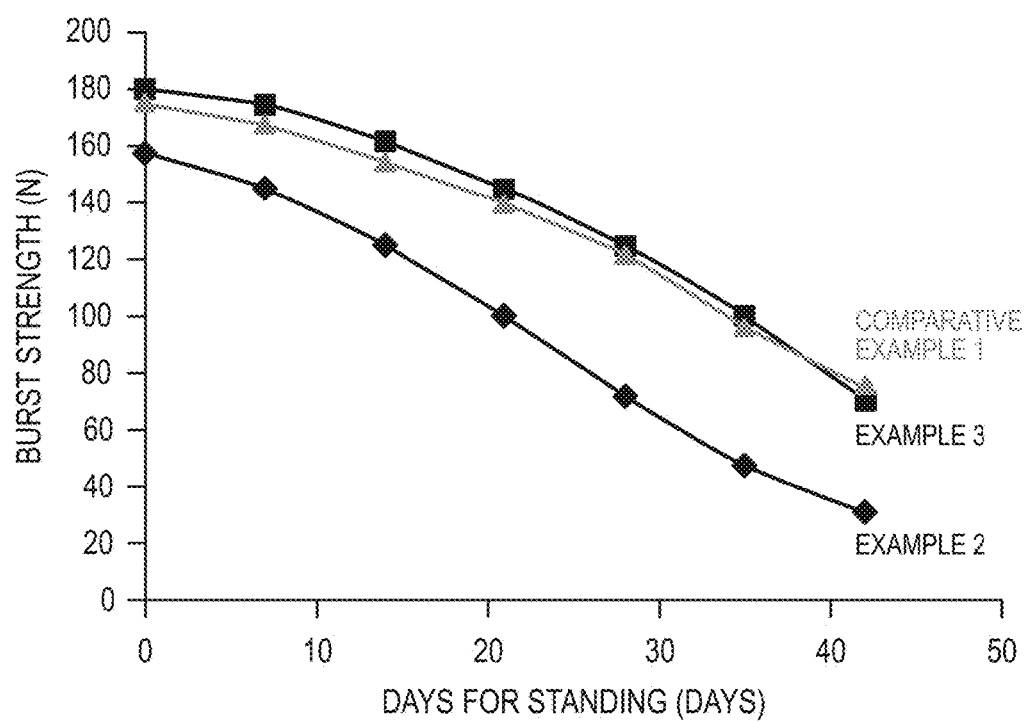

BODY LUMEN GRAFT BASE, PRODUCTION METHOD OF BODY LUMEN GRAFT BASE, AND BODY LUMEN GRAFT USING THE SAME

CROSS REFERENCE TO RELATED APPLICATIONS

This application is a National Stage of International Application No. PCT/JP2014/066588 filed Jun. 23, 2014, claiming priority based on Japanese Patent Application No. 2013-144259 filed Jul. 10, 2013, the contents of all of which are incorporated herein by reference in their entirety.

TECHNICAL FIELD

The present invention relates to a body lumen graft base, a method for producing a body lumen graft base, and a body lumen graft made by using the body lumen graft base.

BACKGROUND ART

In the treatment of aortic diseases (for example, aortic aneurysm or aortic dissection), artificial blood vessel replacement for replacing an affected blood vessel with an artificial blood vessel has been conventionally performed. However, since thoracotomy is required for this treatment, there have been problems that a burden (invasion) on a patient is high and long hospitalization is required. Considering such problems, treatment using a stent graft (stent graft implantation) has been widely used instead of the artificial blood vessel replacement. According to the treatment, a stent graft is encased in a catheter with a small diameter and introduced to an area with aneurysm, and then, the encased stent graft is released from the catheter and expanded, to be placed in an area (affected part) having aneurysm or dissection. Thus, according to the treatment using a stent graft, only a small area is cut in the operation and thoracotomy is not required so that it is a treatment method less invasive than the artificial blood vessel replacement.

For the treatment using a stent graft in an even less invasive manner, it is desirable to decrease a diameter of catheter. For this, it is necessary to use a thin and flexible stent graft base (artificial blood vessel part) to reduce a volume of a stent graft.

For the purpose of solving the above problem, Patent Literature 1 discloses a base fabric for a stent graft which comprises on at least one surface thereof a fiber with a cross-sectional shape which outermost layer has a side approximately parallel to the outermost layer surface, wherein the woven fabric has a yarn density of 150 strands/2.54 cm or more in both longitudinal direction and lateral direction, and a thickness of 1 to 90 μm. The base fabric for a stent graft having such constitutions has thinness, high strength, low permeability and flexibility, and can be inserted into a smaller catheter.

Further, Patent Literature 2 discloses a graft containing a graft fabric which contains a plurality of threads of 5 to 50 denier. It discloses that the graft with such constitution can be encased in an intravascular delivery system with an outer diameter of about 0.06 to 0.27 inch (about 1.52 to 6.8 mm).

CITATION LIST

Patent Literatures

Patent Literature 1: JP 2011-245283 A
Patent Literature 2: JP 2008-505713 A (corresponding to WO 2006/014592 A)

SUMMARY OF INVENTION

Problems to be Solved by the Present Invention

Although the base fabric for a stent graft disclosed in the Patent Literature 1 with low permeability and thinness can be produced by calender treatment so that a size of a catheter can be decreased to a certain level, it is difficult to say that a sufficiently small catheter can be produced.

Further, the graft disclosed in the Patent Literature 2 is described to have low permeability by incorporation of a hydrophilic material. However, there is a problem that when coated with a hydrophilic material, a graft thickness increases or flexibility is impaired. Furthermore, as there is a possibility that the hydrophilic material is peeled off during encasing in a small catheter, it is difficult to say that a sufficiently small catheter can be also produced, similar to the case described above.

Thus, the present invention is accomplished in view of the above circumstances, and has an object to provide a body lumen graft base that can be inserted in a small catheter, a method for producing a body lumen graft base, and a body lumen graft made by using the body lumen graft base.

Another object of the present invention is to provide a body lumen graft base that has, even in the form of a thin film, adequate flexibility and low permeability, a method for producing a body lumen graft base, and a body lumen graft made by using the body lumen graft base.

Still another object of the present invention is to provide a body lumen graft base that has at least one excellent characteristic of thin film thickness, high strength, low permeability, and flexibility, a method for producing a body lumen graft base, and a body lumen graft made by using the body lumen graft base.

Means to Solve the Problem

The present inventors have made intensive studies to solve the aforementioned problems, to find that a base cloth obtained by subjecting a fabric obtained by weaving fibers with a low single fiber fineness in a low density to press treatment, in particular, press treatment using a calender machine, has an excellent function as a body lumen graft base. The present invention has been completed on the basis of the above finding.

That is, the above objects can be achieved by a body lumen graft base having at least one surface of a woven fabric comprising a fiber having a total fineness of 1 to 80 decitex and a single fiber fineness of less than 0.1 decitex subjected to press treatment.

The above objects can also be achieved by a method for producing a body lumen graft base, comprising producing a woven fabric from fibers having a total fineness of 1 to 80 decitex and a single fiber fineness of less than 0.1 decitex, and subjecting at least one surface of the woven fabric to calender treatment.

Advantageous Effect of the Present Invention

The body lumen graft base and body lumen graft of the present invention can be inserted in a small catheter. Furthermore, the body lumen graft base and the body lumen graft of the present invention have adequate flexibility and low permeability even in the form of a thin film.

BRIEF DESCRIPTION OF DRAWINGS

In FIG. 1, 10 represents a device for measuring permeability; 11 represents a sample loading part (hole); 12 represents water; and 13 represents a pressure gauge.

In FIGS. 2A, 2B, and 2C, 2 represents a graft; 3 represents a stent; 4 represents a thread; 5 represents a SUS wire; and 6 represents a PTFE tube (sheath).

In FIG. 3, 20 represents a measurement device; 21 represents a sample loading part (hole); and 22 represents a press.

FIG. 6 is a diagram illustrating a change in burst strength against the number of days of hydrolysis at 90° C. of the graft bases 2 and 3 of Examples 2 and 3 and the comparative graft base 1 of Comparative Example 1.

EMBODIMENTS FOR CARRYING OUT THE PRESENT INVENTION

Figure 1:
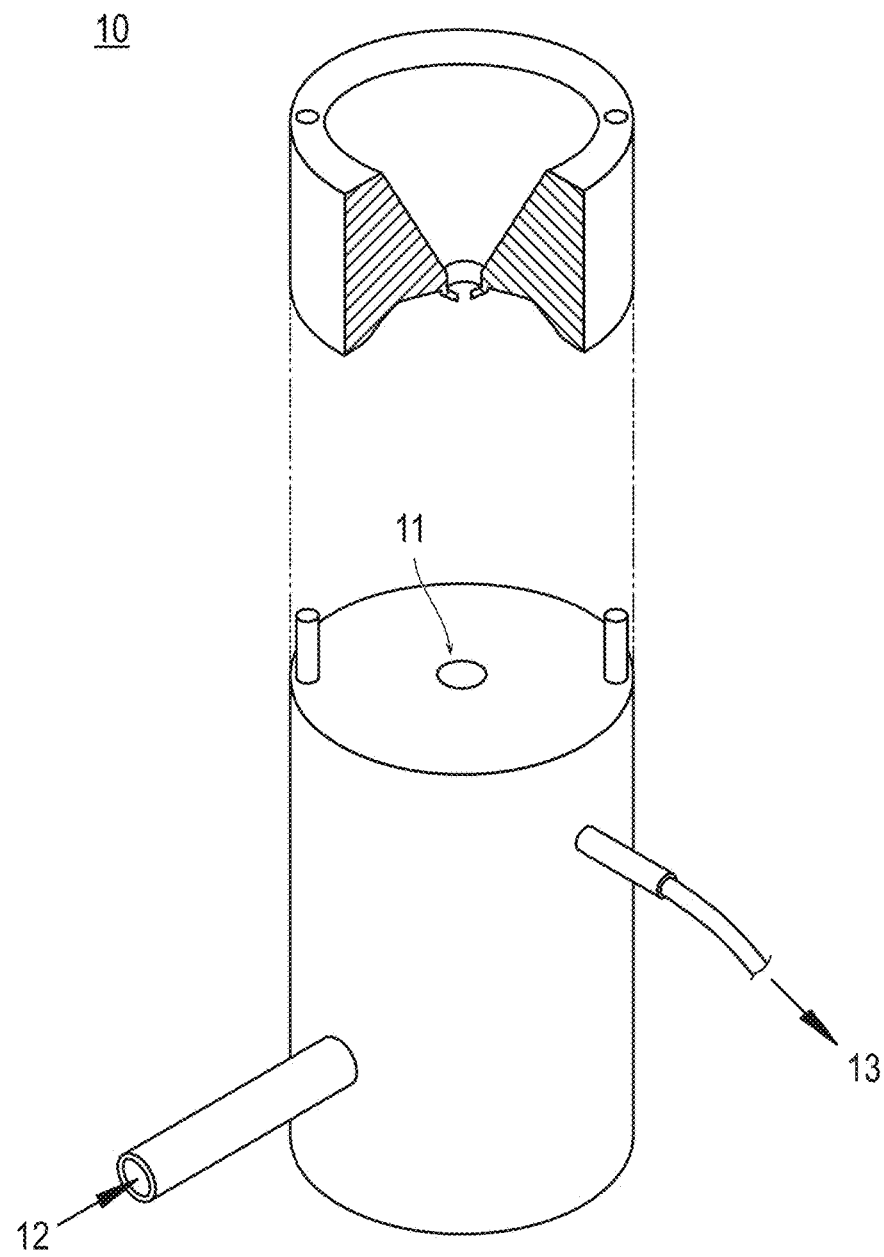
FIG. 1 is a schematic diagram illustrating a device for measuring permeability.

The present invention is provide a body lumen graft base (hereinbelow, it is also simply referred to as a "graft base") having at least one surface of a woven fabric comprising a fiber having a total fineness of 1 to 80 decitex and a single fiber fineness of less than 0.1 decitex subjected to press treatment (hereinbelow, it is also referred to as "calender treatment").

The present invention is also to provide a method for producing a body lumen graft base, which includes producing a woven fabric from fibers having a total fineness of 1 to 80 decitex and a single fiber fineness of less than 0.1 decitex, and subjecting at least one surface of the woven fabric to calender treatment.

The body lumen graft base and the method for producing a body lumen graft base of the present invention can be attained by using a multifilament having a total fineness of 1 to 80 decitex and a single fiber fineness of less than 0.1 decitex, and subjecting a woven fabric having a cover factor of preferably 1300 to 4000 in its woven structure to press treatment, for example, using a calender machine or the like.

It has been also found that a graft cloth with excellent flexibility, permeability, and burst strength can be produced by using a multifilament with small curvature diameter, sufficient strength, and very high fineness to produce a woven fabric with low thickness and subjecting the woven fabric to press treatment to decrease a pore size and porosity between fibers.

The body lumen graft base of the present invention has a feature in being obtained by press treatment (preferably, press treatment by using a calender machine) of a woven fabric (base) which has been obtained by weaving, at a decreased yarn density, a fiber with a low single fiber fineness, that is, less than 0.1 decitex (a total fineness of 1 to 80 decitex). By this, it can be transported within a catheter with a small diameter. Also, since inter-filling of extremely fine fibers which have basically a small pore between fibers can be effectively attained by press processing treatment, desired low permeability can be achieved even with a thin thickness. Further, by using a polymer with high molecular weight, tensile strength and hydrolysis resistance of the fiber itself can be significantly maintained, and good burst strength and good retention rate can be attained.

Further, a surface area of the fiber increases due to decreased single fiber fineness, seam slip-off can be suppressed due to increased abrasion force between fibers, and a deforming force applied to an entire cloth can be absorbed due to micro-rearrangement of fine fibers. Thus, disruption of holes or frame caused by slippage of fibers can be suppressed and blood leakage from sewed part after sewing a stent to the base can be prevented as well.

As described above, the body lumen graft base of the present invention has adequate flexibility and strength and low permeability even if it is thin. For such reasons, the body lumen graft of the present invention using this graft base can be inserted to a small catheter so that treatment using a body lumen graft can be carried out in a less invasive manner.

Hereinbelow, the embodiments of the present invention are described. However, the present invention is not limited to the following embodiments. Furthermore, the dimensional ratio in the drawing is exaggerated for the sake of explanation, and it may be different from the actual ratio.

As described herein, the expression "X to Y" representing a range means "X or more and Y or less", and "weight" and "mass", "% by weight" and "% by mass", and "parts by weight" and "parts by mass" are treated as synonyms, respectively. Furthermore, unless specifically described otherwise, operations and measurements of physical properties or the like are carried out at conditions including room temperature (20 to 25° C.)/relative humidity of 40 to 50%.

The body lumen graft base of the present invention contains a fiber(s) which has a total fineness in the range of 1 to 80 decitex and a single fiber fineness of less than 0.1 decitex. Accordingly, the body lumen graft base of the present invention may contain a fiber(s) other than that (that is, a fiber(s) which has a total fineness more than 80 decitex or a fiber(s) which has a single fiber fineness of 0.1 decitex or more). However, it is preferable that it consists only of a fiber(s) which has a total fineness in the range of 1 to 80 decitex and a single fiber fineness less than 0.1 decitex.

The fiber(s) for constituting the body lumen graft base of the present invention is a multifilament (long fiber). A fabric produced with a multifilament can be easily deformed and rearranged in response to external force, and exhibit softness (flexibility) or wear resistance by local displacement of each filament. For such reasons, a fabric made of a multifilament has excellent wear resistance and flexibility. Meanwhile, the multifilament may be either a zero twist yarn or a twisted yarn, and it may be a false twist yarn given with crimp. Considering the regularity of pores between filament and multifilament, flexibility, decreased film thickness, and low permeability, a zero twist yarn or a false twist yarn is preferable. Furthermore, the fiber(s) constituting the body lumen graft base of the present invention can be either a stretched fiber(s) or a non-stretched fiber(s). Meanwhile, the cross-section of a filament for constituting the multifilament is not particularly limited, and it can be anyone of a circular cross-section, a triangular cross-section, a planar cross-section, and a hollow cross-section. However, from the viewpoint of flexibility and low permeability, a circular cross-section or a planar cross-section is preferable.

As described above, the fiber(s) for constituting the body lumen graft base of the present invention is a multifilament. Here, the number of the filaments for constituting the fiber is not particularly limited. However, from the viewpoint of decreased film thickness and low permeability, the fiber is preferably a multifilament of 100 or more filaments, and more preferably a multifilament of 1000 to 20000 filaments.

The fiber for constituting the body lumen graft base of the present invention has a total fineness of 1 to 80 decitex (dtex) and a single fiber fineness of less than 0.1 decitex (dtex). Here, when the total fineness is less than 1 decitex, it is difficult to handle so that it is impossible to produce a good graft. Furthermore, when the total fineness exceeds than 80 decitex, the body lumen graft base becomes thick and the flexibility is lowered so that a catheter cannot be sufficiently small. The total fineness of the fiber which constitutes the body lumen graft base of the present invention is preferably 10 to 80 decitex, and more preferably 30 to 50 decitex. Further, the single fiber fineness which constitutes the fibers for constituting the body lumen graft base of the present invention is preferably 0.0001 decitex or more and less than 0.1 decitex, more preferably 0.0025 to 0.05 decitex. A body lumen graft base formed of those fibers can have further reduced volume (decreased film thickness) and enhanced flexibility. Meanwhile, it is sufficient that at least one of warp and weft which constitute the body lumen graft base satisfies the above-described total fineness and single fiber fineness. However, it is preferable that both the warp and the weft satisfy the above-described total fineness and single fiber fineness. Furthermore, the total fineness and single fiber fineness of the warp and the weft which constitute the body lumen graft base may be the same or different from each other.

Furthermore, regarding a yarn density of the warp and the weft which constitute the body lumen graft base of the present invention, a yarn density of at least one of warp and weft of a fiber is preferably less than 150 strands/inch, although not particularly limited thereto. By weaving at such low a yarn density, increase in volume of the body lumen graft base (artificial blood vessel part) can be effectively reduced, and also flexibility can be enhanced. Accordingly, by using the body lumen graft base of the present invention (accordingly, the body lumen graft), a size of catheter for encasing can be more decreased. In addition, when a yarn density of one of the warp and the weft satisfies the above yarn density and the other has a yarn density of 150 strands/inch or more, a yarn density of the other weft or warp is, although not particularly limited, preferably 155 to 200 strands/inch, more preferably 170 to 190 strands/inch, from view of improved burst strength or the like. Meanwhile, the yarn density of the warp and the weft is defined in JIS L1096: 2010.

A material of the fiber which constitutes the body lumen graft base of the present invention is not particularly limited, and the same materials as those which have been commonly used for a body lumen graft base can be also used. Specific examples thereof include a polymeric material such as polyester, polyethylene, polytetrafluoroethylene, polyurethane, polyamide (for example, Nylon 6 and Nylon 66), or Nylon. Those materials have excellent biocompatibility. Among them, from the viewpoint of strength (burst strength), polyester, in particular, polyethylene terephthalate (PET), polybutylene terephthalate (PBT), and polytrimethylene terephthalate are preferable, and polyethylene terephthalate (PET) are more preferable.

Here, a molecular weight of the polymeric material is, although not particularly limited, preferably 10,000 to 50,000, more preferably 13,000 to 35,000, in terms of weight average molecular weight. Alternatively, an intrinsic viscosity of the polymeric material is preferably 0.4 to 2.0, more preferably 0.6 to 1.2. The body lumen graft base produced from fibers of a polymeric material having such high molecular weight or intrinsic viscosity (in particular, polyester) can exhibit more excellent strength (burst strength). Accordingly, when the body lumen graft base of the present invention is formed of fibers having relatively low a single fiber fineness, strength (burst strength) of a body lumen graft base to be obtained can be maintained at high level if it is produced from fibers of a polymeric material with high molecular weight (in particular, polyester), which is particularly preferable. Further, when the body lumen graft base is formed of a hydrolysable polymeric material such as polyester, it is more preferable to have high molecular weight from the view of suppression of strength decrease caused by hydrolysis. In particular, considering the hydrolysis resistance, it is particularly preferable that the polymeric material satisfies at least either of weight average molecular weight of 20,000 to 35,000 or intrinsic viscosity of 0.8 to 1.2. A body lumen graft base produced from fibers of a polymeric material having such high molecular weight and/or intrinsic viscosity (in particular, polyester) is less likely to suffer from strength decrease that is caused by hydrolysis. Meanwhile, as described herein, the "weight average molecular weight" is a value which is measured by gel permeation chromatography (GPC) using GPC device under following conditions using polymethyl methacrylate as a standard.

[Chemical Formula 1]
<Conditions for Measuring Weight Average Molecular Weight>
Device: Semimicro GPC System LC-20AD (manufactured by Shimadzu Corporation)
Detector: Shodex RI-104 (manufactured by Showa Denko K.K.)
Column: Shodex GPC LF-404 (manufactured by Showa Denko K.K.)
Column temperature: 40° C.
Solvent for mobile phase: 5 mmol/L $CF_3COONa$/1,1,1,3,3,3-hexafluoro-2-propanol (HFIP)
Flow rate: 0.45 ml/min
Injection amount: 20 μl
Sample preparation: To about 3 mg of a sample for measurement (polymeric material), 3 mL of flow rate indicator solution (mobile phase solvent containing 1% ethyl acetate) is added, dissolved under heating, and filtered through a 0.45 μm PTFE membrane filter.

As used herein, the "intrinsic viscosity" is a value that is measured at concentration of 1.2 g/100 ml and temperature of 35° C. in an o-chlorophenol solution.

The method for producing a fiber(s) with a specific total fineness and single fiber fineness is not particularly limited. The production can be made by direct spinning or composite spinning using a sea-island type or fiber-splitting type composite spinneret to make a woven fabric, followed by making it ultrafine. For example, a method described in WO 2005/095686 A1 is preferably used. Namely, the fiber having a specific total fineness and single fiber fineness according to the present invention can be produced by melt-extracting a polymer for a sea part comprising an easily soluble polymer and a polymer for island parts comprising a hardly soluble polymer having a lower melt viscosity than that of the easily soluble polymer, through a spinneret for an islands-in-sea type composite fiber, to a islands-in-sea type composite filament, and taking up the extruded islands-in-sea type composite filament. In the method, examples of the island parts include, although not particularly limited, the material which constitutes the fibers for constituting the body lumen graft base described above. As for the sea part, although any polymer can be used, a polymer having a ratio in dissolving rate to the island-part polymer of not less than 200 more is preferably used. Examples thereof include polyester, polyamide, polystyrene and polyethylene that have fiber formability. For example, polylactic acid, super high molecular weight polyalkyleneoxide-condensate polymers, polyethyleneglycol compound-copolymerized polyesters, and copolymerized polyesters of polyethylene glycol compounds with 5-sodium sulfoisophthalic acid, which is a polymer easily soluble in an aqueous alkali solution, are preferable. Further, Nylon 6 is soluble in formic acid, and a polystyrene-polyethylene copolymer is very soluble in an organic solvent such as toluene. Of these, in order to make the alkali easy solubility and the islands-in-sea cross section-formability of the sea part polymer compatible, a preferred example of the polyester polymer is a polyethylene terephthalate polyester copolymer having an intrinsic viscosity of 0.4 to 0.6 and obtained by copolymerizing 6 to 12% by mole of 5-sodium sulfoisophthalate and 3 to 10% by weight of a polyethylene glycol having a molecular weight of 4,000 to 12,000. 5-Sodium sulfoisophthalate herein contributes to improve the hydrophilicity and melt viscosity of the copolymer thus obtained, and the polyethylene glycol (PEG) herein improves the hydrophilicity of the copolymer. In addition, a PEG having a larger molecular weight shows a greater effect of increasing hydrophilicity thought to be caused by the high order structure. On the other hand, such a PEG has lowered reactivity with the acid part, and the reaction product thus obtained becomes in a blend form, which is not preferable in view of heat resistance and spinning stability. Further, when the copolymerized amount of the PEG is 10% by weight or more, the copolymer thus obtained can hardly achieves the object of the present invention, because PEG inherently has a function of lowering the melt viscosity. Accordingly, both components are preferably copolymerized in the above range.

For the islands-in-sea type composite fiber of the present invention comprising the above sea part polymer and the above island part polymer, a melt viscosity of the sea part polymer during melt spinning is preferably higher than that of the island part polymer. In such a relationship, even in the case where a composite mass ratio of the sea part is as low as less than 40%, formation of a fiber different from the islands-in-sea type composite fiber by mutually bonding the island parts or mutually bonding most of the island parts can be suppressed or prevented.

A melt viscosity ratio (sea part/island parts) is preferably 1.1 to 2.0, more preferably 1.3 to 1.5. In such a ratio, mutually bonding of the island parts in the stable melt spinning of a process can be suppressed or prevented to perform the spinning step stably.

When the number of island parts is large, productivity during the production of fine fibers by dissolving and removing the sea part would increase, and a fine fiber thus obtained would be significantly thin, to manifest softness, smoothness, luster, and the like which is specific to ultrafine fiber. Thus the number of island parts is preferably 25 or more, more preferably 100 or more, still more preferably 500 or more. If the number of island parts is less than 25, a high multifilaments yarn composed of ultrafine fibers could not be obtained even when the sea part is dissolved and removed. Meanwhile, when the number of the island parts excessively increases, not only production cost of the spinneret would be too high, but also working precision itself of the spinneret would be lowered. Thus the number of the island parts is preferably made 1,000 or less.

Further, it is necessary that a thickness of the island parts be 10 to 1,000 nm, and preferably 100 to 700 nm. By the thickness of the island within such a range, a fiber structure itself can be stabilized to stabilize physical properties and fiber form. At the same time, softness and feel specific to the ultrafine fiber can be attained. Furthermore, each of the island parts in a cross-sectional profile of the composite fiber preferably has a uniform thickness, because a high multifilaments yarn composed of fine fibers obtained by removing the sea part show more improved quality and durability.

Furthermore, for the islands-in-sea type composite fiber of the present invention, a weight ratio of the sea part to the island parts (sea part:island parts) per composite fiber is preferably in the range of 40:60 to 5:95, particularly preferably 30:70 to 10:90. In such a ratio, a thickness of the sea part between the island parts can be decreased, to easily dissolve and remove the sea part, and to easily convert the island parts into fine fibers. When the ratio of the sea part exceeds 40%, the thickness of the sea part would be underly large. On the other hand, when the ratio is less than 5%, the amount of the sea part would be underly small to induce mutual bonding of the island parts.

For the islands-in-sea type composite fiber of the present invention, an elongation at break of the island parts is preferably greater than that of the sea part. Moreover, in the case where a cross-sectional thickness (r) of the island parts, and a smallest intervals (Smin) between the island parts located on four straight lines which pass through the center of the cross-sectional profile of the composite fiber, at angular intervals of 45 degrees, and also a cross sectional thickness (R) of the composite fiber and a largest intervals (Smax) of the island parts located on the four strength lines satisfy the following requirements (I) and (II), fine fibers having a mechanical strength that withstand practical uses can be obtained.

[Numerical formula 1]

$$0.001 \leq Smin/r \leq 1.0 \qquad \text{Formula (I):}$$

[Numerical formula 2]

$$Smax/R \leq 0.15 \qquad \text{Formula (II):}$$

Meanwhile, when a central portion of the composite fiber is formed of a sea part in the measurement of intervals among the island parts, an interval between two island parts that are adjacent to each other through the central portion is excluded. From the above, it is preferable that $0.01 \leq Smin/r \leq 0.7$, and $Smax/R \leq 0.08$. When the Smin/r is 1.0 or less, or when the Smax/R is 0.15 or less, since a high speed spinnability during the production of the composite fiber can be attained, or a draw ratio can be increased, physical properties of the drawn yarn of the islands-in-sea type composite fiber thus obtained, and mechanical strength of the fine fibers obtained by dissolving and removing the sea part can be improved. When the Smin/r is 0.001 or more, mutually stick (stalemate) of the island parts can be effectively suppressed and prevented.

Furthermore, for the islands-in-sea type composite fiber of the present invention, an interval between the island parts adjacent to each other is 500 nm or less, and preferably in the range of 20 to 200 nm. When the interval between the island parts is 500 nm or less, dissolution of the island parts rarely proceeds or does not proceed during dissolution and removal of the sea part occupying the intervals. As a result, uniformity of the island parts can be secured, and fine fibers formed out of the island parts can be advantageously put into practical use.

The islands-in-sea type composite fiber can be easily produced by, for example, the process as below. To be specific, first, a polymer that has a high melt viscosity and is easily soluble, and a polymer that has a low melt viscosity and is hardly soluble are melt spun in such a manner that the former polymer forms a sea part and the latter polymer forms island parts. The relationship between the melt viscosity of the sea part and that of the island parts herein is important. When a content of the sea part is lowered to decrease an interval between the island parts, the sea part would come to flow at a high speed through part of the flow paths between the island parts within the melt spinning spinneret of the composite fiber in the case where the melt viscosity of the sea part is low. As a result, mutual bonding between the island parts unpreferably would tend to take place.

In a stress-strain curve at room temperature of the islands-in-sea type composite undrawn fiber for fine fibers, a yield point corresponding to a partial break of the sea part is sometimes manifested. This is a phenomenon observed when the orientation of the sea part proceeds due to the fast solidification of the sea part in comparison with the island parts, while the orientation of the island parts is low due to the influence of the sea part. A first yield point signifies a partial breaking point of the sea part (the point being defined as an elongation at partial break IP %), and the island parts showing a low orientation are elongated after the yield point. Moreover, both the island parts and the sea part are broken at the breaking point in the stress-strain curve (the point being defined as an elongation at total break It %). These phenomena can be explained from the fact that the first yield point is transferred more to the initial stage when the spinning speed is increased. An ordinary stress-strain curve may of course be shown in place of the stress-strain curve at room temperature.

Figure 2C:
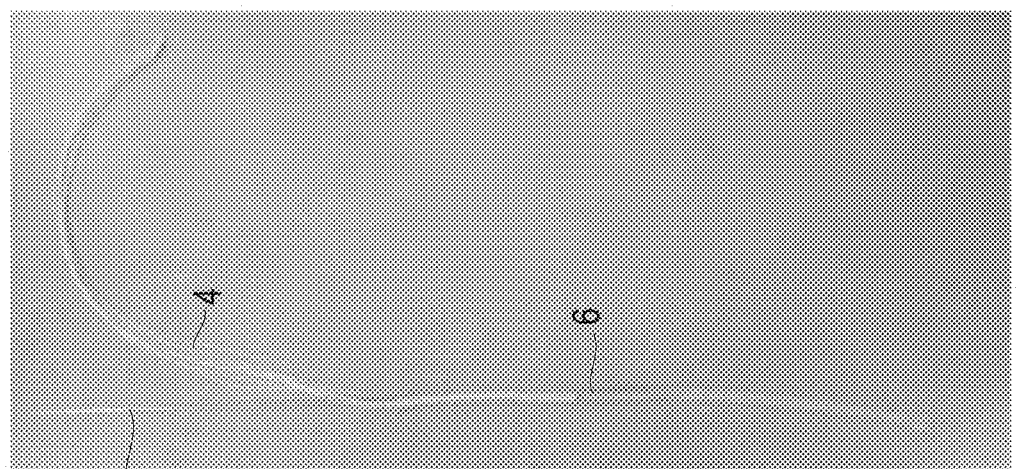
FIGS. 2A, 2B, and 2C are diagrams illustrating the measurement of a size of sheath to be adapted.

As the spinneret used for melt spinning an islands-in-sea type composite fiber of the present invention, a group of hollow pins, a group of fine pores, for forming island parts can be suitably used. For example, any spinneret may be used as long as island parts extruded through hollow pins or fine pores and sea part flows supplied from flow paths designed to make the sea part flows fill the gaps between the island parts can be combined, and the combined flow can be gradually made thin and extruded through an extrusion orifice to form an islands-in-sea type composite fiber. For example, the spinneret described in FIG. 1 and FIG. 2 of WO 2005/095686 A1 can be preferably used.

The extruded islands-in-sea type composite fiber is solidified with a cooling wind. A spinning speed is not particularly limited, but considering the productivity and spinning stability, the fiber is wound at a speed of preferably 400 to 6000 m/minute, and more preferably at speed of 1000 to 3500 m/minute.

The undrawn fiber thus obtained may be additionally drawn to give a drawn composite fiber having a tensile strength, an elongation at break and a thermal shrinkage that are desired. Alternatively, the undrawn fiber may also be taken up with a roller at a constant speed without winding, subsequently drawn, and then wound. Specifically, the undrawn fiber is preferably preheated with a preheating roller at a temperature of 60 to 190° C., preferably 75 to 180° C., and drawn at a draw ratio of 1.2 to 6.0, preferably 2.0 to 5.0, and then subjected to heat-setting on a heat setting roller at a temperature of 120 to 220° C., preferably 130 to 200° C. When the preheating temperature would be insufficient, an aimed high draw ratio could not be attained. When the setting temperature is too low, the shrinkage of the drawn fiber thus obtained would be unpreferably excessively high. Moreover, when the setting temperature is excessively high, the drawn fiber thus obtained would have significantly poor physical properties, which is unpreferable.

In the production process of the present invention, in order to produce an islands-in-sea type composite fiber having a particularly fine island part thickness with great efficiency, it is preferred to employ a fluidization drawing step that makes a fiber thickness alone fine without changing the fiber structure, prior to neck drawing (orientation crystallization drawing) involving conventional so-called orientation crystallization. In order to make the fluidization drawing easy herein, it is preferred to uniformly preheat the fiber with a water medium having a large heat capacity, and draw at a low speed. When such a procedure is conducted, the fiber structure is likely to forma fluidized state during drawing, and the fiber can be easily drawn without developing a fine fiber structure. When the pre-fluidization drawing is to be conducted, it is particularly preferred that both the sea part polymer and the island part polymer be a polymer having a glass transition temperature of 100° C. or less. Of polymers, polyesters such as PET, PBT, polylactic acid and polytrimethylene terephthalate are appropriately used. Specifically, the taken-up composite fiber is preferably pre-fluidization drawn at a draw ratio of 10 to 30, a feed speed of 1 to 10 m/min and a winding speed of 300 m/min or less, 10 to 300 m/min in particular while the composite fiber is being uniformly heated by immersing the composite fiber in a hot water bath at a temperature of 60 to 100° C., preferably 60 to 80° C. When the preheating temperature is inadequate and the drawing speed is too high, an aimed high draw ratio could not be attained.

The pre-drawn fiber having been pre-drawn in the above-fluidized state is subjected to orientation crystallization drawing at a temperature of 60 to 150° C. in order to improve mechanical properties such as strength and elongation. When drawing is conducted at a temperature outside the above range, physical properties of the fiber thus obtained would become unsatisfactory. Meanwhile, the above draw ratio can be determined depending on conditions such as melt spinning conditions, fluidization drawing conditions and orientation crystallization drawing conditions. However, it is generally preferred to set the draw ratio in the range of 0.6 to 0.95 that is a maximum possible draw ratio under the orientation crystallization drawing conditions.

A CV value that represents a variability in thickness of individual fine fibers having a thickness of 10 to 1,000 nm and obtained by dissolving and removing the sea part from the islands-in-sea type composite fiber of the present invention is preferably 0 to 25%, more preferably 0 to 20% and still more preferably 0 to 15%. A low CV % value signifies that variability in thickness is small. The use of a fine fiber bundle having a decreased variability in an individual fiber thickness makes it possible to adjust the fiber thickness of the individual fine fibers in the order of nanometers.

The fine fiber bundle obtained by dissolving and removing the sea part from the islands-in-sea type composite fiber of the present invention and composed of fine fibers having a thickness of 10 to 1,000 nm preferably has a tensile strength of 1.0 to 6.0 cN/dtex, an elongation at break of 15 to 60% and a dry heat shrinkage at 150° C. of 5 to 15%.

The fabric according to the present invention is a cloth made of a fabric containing (preferably, consisting of) the fiber (yarn), as described above or to be produced by the method described above, and the body lumen graft base of the present invention consists of the fabric. The cloth structure is not particularly limited, and the same structure as the structure used for a common graft base like a knitted fabric, a non-woven fabric can be also used. However, from the viewpoint of decreased thickness and strength (burst strength), it is preferably a woven fabric. The fabric construction is not particularly limited, either. The same construction as the construction used for a common graft base can be also used. Specific examples thereof include plain weave, twill weave, satin weave, and double weave. Among them, from the viewpoint of strength and decreased thinness, plain weave and twill weave are preferable. Plain weave is more preferable. Cloth shape is not particularly limited, either. It can be a tubular kinitted fabric as well as a common planar fabric.

A method for producing the fabric of the present invention is not particularly limited, and any known method can be used. For example, a method of having plane weave to place 1 to 4 wefts per warp can be used. A device for producing the fabric of the present invention is not particularly limited, either, and a known device can be similarly used. Examples of the device which can be used include water jet weaving machines, air jet weaving machines, shuttless weaving machines such as needle weaving machine, Fly shuttle weaving machines, tappet weaving machines, Dobby weaving machines, Jacquard looms, and the like may be used. After weaving, as needed, scouring and relaxation treatment can be performed to perform heat set by a tenter and/or the like.

The fabric of the present invention is subjected to press treatment by a calender machine. In this case, a surface of the calender is preferably heated at a temperature higher than a glass transition temperature or a softening point of a polymer constituting the fiber. According to the calender treatment, filling action between filaments and multifilaments is generated so that the permeability can be suppressed at low level. A heating treatment is not particularly limited, but the treatment is preferably performed while heating the calender to a temperature of 120 to 180° C. Furthermore, a nip pressure is preferably 10 to 100 kg/cm and a treatment speed is preferably 2 to 30 m/min.

In the present invention, it is possible that at least one surface of the fabric of the present invention is covered, either before or after the calender treatment, by coating with a film like thin polymeric material, a porous film, or a non-woven fabric. By this, permeability can be further lowered to suppress or prevent blood leakage more efficiently.

A cover factor (amount of yarns per unit area) of the fabric of the present invention is, although not particularly limited, preferably 1300 to 4000, more preferably 1400 to 3500, and even more preferably 1500 to 3000, from the viewpoint of having decreased thickness, low permeability, and strength (burst strength). Within the range, the fabric of the present invention can exhibit sufficiently low permeability and strength (burst strength) while having a thin thickness. As described herein, a cover factor is calculated according to the following formula (III).

[Numerical formula 3]

$$CF = \sqrt{A} \times N + \sqrt{B} \times M \quad \text{Formula (III)}$$

With the proviso that CF represents a cover factor;
A represents fineness (decitex) of warp;
B represents fineness (decitex) of weft;
N represents the number of warp (strands/inch); and
M represents the number of weft (strands/inch).

A thickness of the fabric of the present invention is, although not particularly limited, preferably as thin as possible. Specifically, the thickness of the fabric of the present invention is preferably 1 to 90 µm, more preferably 20 to 80 µm, and particularly preferably 30 to 70 µm. With such a thickness, the body lumen graft base of the present invention (thus the body lumen graft) can be folded to have a small size and easily inserted to a thin catheter with an inner diameter of 12 Fr or less (in particular, 11 Fr or less). With such a thickness, the body lumen graft base of the present invention (thus the body lumen graft) can also have sufficient strength and flexibility.

The body lumen graft base of the present invention has low permeability. Specifically, the body lumen graft base of the present invention preferably has permeability of 0 to 500 mL/min/cm$^2$, more preferably 0 to 300 mL/min/cm$^2$, and particularly preferably 0 to 200 mL/min/cm$^2$. With such permeability, blood leakage from a graft base can be effectively suppressed or inhibited. Meanwhile, the "permeability" as used herein means a value that is defined by the following example.

The body lumen graft base of the present invention of the present invention has high strength. Specifically, the body lumen graft base of the present invention preferably has burst strength of 100 to 300 N, and more preferably 150 to 200 N. With such strength, the body lumen graft which is produced by using the body lumen graft base of the present invention can sufficiently occlude aneurysm after being placed (fixed) in the aneurysm t lower a pressure of blood flow into the aneurysm, thereby reducing a size of the aneurysm. Meanwhile, the "burst strength" as used herein means a value that is defined by the following example.

The body lumen graft base of the present invention has a low seam slippage property. Specifically, the seam slippage property (enlarged needle hole formed by sewing) is 1.5 mm or less both in the length direction and the width direction. Furthermore, the mean value is preferably 0 to 1.5 mm, and more preferably 0 to 1.2 mm. With a graft base having such low seam slippage property, enlargement of a needle hole formed by sewing can be reduced to effectively suppress or prevent blood leakage from a graft base. Meanwhile, the "seam slippage property" as used herein means a value that is defined by the following example (see, the section for evaluation of an enlarged needle hole formed by sewing).

Accordingly, the body lumen graft base of the present invention can be preferably applied to a body lumen graft. Specifically, the present invention also provides a body lumen graft which includes the body lumen graft base of the present invention or a body lumen graft base produced by the method of the present invention, and a stent.

The body lumen graft of the present invention can be used for a graft base of a body lumen graft (artificial blood vessel part), an artificial blood vessel, an artificial bronchus, an artificial bronchial tube, an artificial esophagus, or the like. It can be advantageously used for a graft base of a body lumen graft (artificial blood vessel part) or an artificial blood vessel. Meanwhile, the body lumen graft base of the present invention can be also used for a medical application other than those described above. Among the above applications, the body lumen graft base of the present invention can be directly applied to an artificial blood vessel. Hereinbelow, a preferred embodiment wherein the body lumen graft base of the present invention is applied to a graft base of a body lumen graft (artificial blood vessel part) is described, but the present invention is not limited thereto.

The body lumen graft is a kind of an artificial blood vessel having a spring-shaped metal (stent part) referred to as a stent attached to an artificial blood vessel, and used after being compressed and encased in a small catheter. The body lumen graft base of the present invention can be used for an artificial blood vessel part of a body lumen graft (graft base). Furthermore, the stent part can be a self-expanding type stent, a balloon expanding type stent, or a hybrid type stent combining them (that is, a combination type of balloon-expandable part and a self-expandable part). A material for the stent is not particularly limited, and examples of the material that can be preferably used include a metal material such as stainless steel (for example, SUS304, SUS316L, SUS420J2, or SUS630), gold, platinum, silver, copper, nickel, cobalt, titanium, iron, aluminum, tin, and their alloys such as nickel-titanium alloy, cobalt-chrome alloy, or zinc-tungsten alloy. In the body lumen graft of the present invention, at least one stent is fixed to the body lumen graft base of the present invention by sewing yarn or the like.

Further, in the case of using the body lumen graft base of the present invention for a body lumen graft, a method for applying it to a patient is not particularly limited, and a known method can be similarly used. For example, the body lumen graft is folded to have a small size and encased in a catheter. Here, a size of a catheter is not particularly limited, but an inner diameter is 12 Fr or less (3 Fr=1 mm), in particular, the inner diameter is preferably 11 Fr or less. Accordingly, it can be less invasive for a patient. Next, after cutting 4 to 5 cm of a groin area of a patient to expose femoral artery, the catheter is inserted to a femoral artery and introduced to an area with aneurysm by X-ray fluoroscopy. After the body lumen graft is confirmed to span the aneurysm, the body lumen graft is released and expanded to be placed (fixed) across the aneurysm. After the body lumen graft is confirmed to be placed (fixed) correctly across the aneurysm, the catheter is pulled out and the cut area in the femoral artery is closed. According to this method, the aneurysm can be occlude by the body lumen graft, to lower a pressure of blood flow into the aneurysm, thereby reducing a size of the aneurysm. Since the method does not require a laparotomy or thoracotomy and can make an incision site small, it is a minimally invasive treatment with very little burden on a body of a patient.

EXAMPLES

The effect(s) by the present invention is described by way of the following Examples and Comparative Examples shown below. However, the technical scope of the present invention is not limited to the following examples.

Example 1

A multifilament fiber having a total fineness of 56 dtex and a single filament number of 36, which is composed of as a single filament islands-in-sea type composite fibers having the islands parts made of polyethylene terephthalate (PET) with an intrinsic viscosity of 0.6, having a ratio of sea part:island parts of 30:70 and the number of island parts of 25, was used both as warp and weft to be weaved into a plain weave having a warp density of 145 strands/inch and a weft density of 118 strands/inch (base 1). To remove the sea part of the islands-in-sea type composite fiber from the resuntant base 1, the base 1 is reduced by 32% with a 2.5% NaOH aqueous solution at 60° C., and then subjected to wet heat treatment and dry heat treatment by a conventional method. The base thus obtained (base 2) was subjected to press treatment using a common calender machine at temperature of 160° C., a nip pressure of 40 kg/cm, and a speed of 5 m/min, to obtain a graft base 1. For the graft base 1 thus obtained, a fabric surface and a cross-section of a warp and a weft were observed with a scanning type electron microscope SEM, to confirm that the sea parts were completely dissolved and removed, a total fineness of the warp was 39 dtex, and a total fineness of the weft was 39 dtex. From the total fineness values and the number of single filaments, that is, 900 (a value obtained by multiplying the number of islands in the single filament of the islands-in-sea type composite fiber by the number of single filaments of the islands-in-sea type composite fiber), a single fiber fineness was calculated to be 0.043 dtex for both of the warp and the weft. Furthermore, a weight average molecular weight of the constituting polyethylene terephthalate was measured, to be found to be 14500. With regard to the graft base 1, a longitude density (warp density) was 183 strands/inch, a latitude density (weft density) was 129 strands/inch, a cover factor CF was 1948, a thickness was 68 μm, permeability was 57 mL/min/cm², and burst strength was 178 N. Further, an adaptation sheath diameter in a state in which the graft base 1 is provided with a stent was 11 Fr. Seam slippage property was 1.4 mm and 0.8 mm in the height direction and the width direction, respectively, and there was no enlargement of needle hole formed by sewing of the base.

Example 2

A multifilament fiber having a total fineness of 56 dtex and a single filament number of 10, which is composed of as a single filament islands-in-sea type composite fibers having the islands parts made of polyethylene terephthalate (PET) with an intrinsic viscosity of 0.6, having a ratio of sea part:island parts of 30:70 and the number of island parts of 836, was used both as warp and weft to be weaved into a plain weave having a warp density of 145 strands/inch and a weft density of 118 strands/inch (base 3). To remove the sea part of the islands-in-sea type composite fiber from the resuntant base 3, the base 3 is reduced by 32% with a 2.5% NaOH aqueous solution at 60° C., and then subjected to wet heat treatment and dry heat treatment by a conventional method. The base thus obtained (base 4) was subjected to press treatment using a common calender machine at temperature of 160° C., a nip pressure of 40 kg/cm, and a speed of 5 m/min, to obtain a graft base 2. For the graft base 2 thus obtained, a fabric surface and a cross-section of a warp and a weft were observed with a scanning type electron microscope SEM, to confirm that the sea parts were completely dissolved and removed, a total fineness of the warp was 39 dtex, and a total fineness of the weft was 39 dtex. From the total fineness values and the number of single filaments, that is, 8360 (a value obtained by multiplying the number of islands in the single filament of the islands-in-sea type composite fiber by the number of single filaments of the islands-in-sea type composite fiber), a single fiber fineness was calculated to be 0.0047 dtex for both of the warp and the weft. Furthermore, a weight average molecular weight of the constituting polyethylene terephthalate was measured, to be found to be 14500. With regard to the graft base 2, a longitude density (warp density) was 177 strands/inch, a latitude density (weft density) was 128 strands/inch, a cover factor CF was 1905, a thickness was 65 μm, permeability was 168 mL/min/cm², and burst strength was 157 N. Further, an adaptation sheath diameter in a state in which the graft base 2 is provided with a stent was 11 Fr. Seam slippage property was 1.2 mm and 1.0 mm in the height direction and the width direction, respectively, and there was no enlargement of needle hole formed by sewing of the base.

Example 3

A multifilament fiber having a total fineness of 56 dtex and a single filament number of 10, which is composed of as a single filament islands-in-sea type composite fibers having the islands parts made of polyethylene terephthalate (PET) with an intrinsic viscosity of 1.0, having a ratio of sea part:island parts of 30:70 and the number of island parts of 836, was used both as warp and weft to be weaved into a plain weave having a warp density of 145 strands/inch and a weft density of 118 strands/inch (base 5). To remove the sea part of the islands-in-sea type composite fiber from the resuntant base 5, the base 5 is reduced by 32% with a 2.5% NaOH aqueous solution at 60° C., and then subjected to wet heat treatment and dry heat treatment by a conventional method. The base thus obtained (base 6) was subjected to press treatment using a common calender machine at temperature of 160° C., a nip pressure of 40 kg/cm, and a speed of 5 m/min, to obtain a graft base 3. For the graft base 3 thus obtained, a fabric surface and a cross-section of a warp and a weft were observed with a scanning type electron microscope SEM, to confirm that the sea parts were completely dissolved and removed, a total fineness of the warp was 39 dtex, and a total fineness of the weft was 39 dtex. From the total fineness values and the number of single filaments, that is, 8360 (a value obtained by multiplying the number of islands in the single filament of the islands-in-sea type composite fiber by the number of single filaments of the islands-in-sea type composite fiber), a single fiber fineness was calculated to be 0.0047 dtex for both of the warp and the weft. Furthermore, a weight average molecular weight of the constituting polyethylene terephthalate was measured, to be found to be 24700. With regard to the graft base 3, a longitude density (warp density) was 185 strands/inch, a latitude density (weft density) was 133 strands/inch, a cover factor CF was 1986, a thickness was 69 μm, permeability was 128 mL/min/cm$^2$, and burst strength was 180 N. Further, an adaptation sheath diameter in a state in which the graft base 3 is provided with a stent was 11 Fr. Seam slippage property was 1.0 mm both in the height direction and the width direction, and there was no enlargement of needle hole formed by sewing of the base.

Comparative Example 1

A polyethylene terephthalate (PET) multifilament fiber having a total fineness of 44 dtex (a single fiber fineness=1.6 dtex, formed of polyethylene terephthalate (PET) with an intrinsic viscosity of 0.6) was used to be weaved into a plain weave having a warp density of 163 strands/inch and a weft density of 124 strands/inch (comparative graft base 1). A weight average molecular weight of the constituting polyethylene terephthalate was measured, to be found to be 14900. With regard to the obtained comparative graft base 1, a cover factor CF was 1904, a thickness was 120 μm, permeability was 200 mL/min/cm$^2$, and burst strength was 176 N. Further, an adaptation sheath diameter in a state provided with the comparative graft base 1 was 13 Fr. Seam slippage property was not determined (N/A), but there was almost no enlargement of needle hole formed by sewing of the base.

Comparative Example 2

A polyethylene terephthalate (PET) multifilament fiber having a total fineness of 44 dtex (a single fiber fineness=1.6 dtex, formed of polyethylene terephthalate (PET) with an intrinsic viscosity of 0.6) was used to be weaved into a plain weave having a warp density of 163 strands/inch and a weft density of 124 strands/inch (comparative graft base 2). A weight average molecular weight of the constituting polyethylene terephthalate was measured, to be found to be 14900. The comparative graft base 2 thus obtained was subjected to press treatment using a common calender machine at temperature of 150° C., a nip pressure of 100 kg/cm, and a speed of 10 m/min, to obtain a comparative graft base 2. With regard to the comparative graft base 2, a cover factor CF was 1904, a thickness was 80 μm, permeability was 49 mL/min/cm$^2$, and burst strength was 176 N. Further, an adaptation sheath diameter in a state provided with the comparative graft base 2 was 13 Fr. Seam slippage property was not determined (N/A), but there was almost no enlargement of needle hole formed by sewing of the base.

Comparative Example 3

A polyethylene terephthalate (PET) multifilament fiber having a total fineness of 56 dtex (a single fiber fineness=2.0 dtex, formed of polyethylene terephthalate (PET) with an intrinsic viscosity of 0.6 (weight average molecular weight: about 15000)) was used as a warp and a polyethylene terephthalate (PET) multifilament fiber having a total fineness of 84 dtex (a single fiber fineness=2.0 dtex, formed of polyethylene terephthalate (PET) with an intrinsic viscosity of 0.6) was used as a weft, to be weaved into a plain weave having a warp density of 112 strands/inch and a weft density of 84 strands/inch (comparative graft base 3). A weight average molecular weight of the constituting polyethylene terephthalate was measured, to be found to be 15000. The comparative graft base 3 thus obtained was subjected to press treatment using a common calender machine at temperature of 150° C., a nip pressure of 100 kg/cm, and a speed of 10 m/min, to obtain a comparative graft base 3. With regard to the comparative graft base 3, a cover factor CF was 1608, a thickness was 62 μm, permeability was 20 mL/min/cm$^2$. Burst strength was 149 N. Further, an adaptation sheath diameter in a state provided with the comparative graft base 3 was 11 Fr. Seam slippage property was 1.9 mm and 2.0 mm in the height direction and the width direction, respectively, and enlargement of needle hole could be confirmed.

Comparative Example 4

A polyethylene terephthalate (PET) multifilament fiber having a total fineness of 44 dtex (a single fiber fineness=2.2 dtex, formed of polyethylene terephthalate (PET) with an intrinsic viscosity of 1.0) was used to be weaved into a plain weave having a warp density of 129 strands/inch and a weft density of 119 strands/inch (comparative graft base 4). The comparative graft base 4 thus obtained was subjected to press treatment using a common calender machine at temperature of 160° C., a nip pressure of 40 kg/cm, and a speed of 5 m/min, to obtain a comparative graft base 4. A weight average molecular weight of the constituting polyethylene terephthalate was measured, to be found to be 25000. With regard to the comparative graft base 4, a cover factor CF was 1645, a thickness was 72 permeability was 371 mL/min/cm$^2$. Burst strength was 153 N. Further, an adaptation sheath diameter in a state provided with the comparative graft base 4 was 11 Fr. Seam slippage property was 1.4 mm and 1.7 mm in the height direction and the width direction, respectively, and enlargement of needle hole could be confirmed.

Comparative Example 5

A multifilament fiber having a total fineness of 56 dtex and a single filament number of 10, which is composed of as a single filament islands-in-sea type composite fibers having the islands parts made of polyethylene terephthalate (PET) with an intrinsic viscosity of 0.6, having a ratio of sea part:island parts of 30:70 and the number of island parts of 836, was used both as warp and weft to be weaved into a plain weave having a warp density of 145 strands/inch and a weft density of 118 strands/inch (base 7). To remove the sea part of the islands-in-sea type composite fiber from the resuntant base 7, the base 7 is reduced by 32% with a 2.5% NaOH aqueous solution at 60° C., and then subjected to wet heat treatment and dry heat treatment by a conventional method, obtain a comparative graft base 5. For the comparative graft base 5 thus obtained, a fabric surface and a cross-section of a warp and a weft were observed with a scanning type electron microscope SEM, to confirm that the sea parts were completely dissolved and removed, a total fineness of the warp was 39 dtex, and a total fineness of the weft was 39 dtex. From the total fineness values and the number of single filaments, that is, 8360 (a value obtained by multiplying the number of islands in the single filament of the islands-in-sea type composite fiber by the number of single filaments of the islands-in-sea type composite fiber), a single fiber fineness was calculated to be 0.0047 dtex for both of the warp and the weft. Furthermore, a weight average molecular weight of the constituting polyethylene terephthalate was measured, to be found to be 14500. With regard to the comparative graft base 5, a warp density was 165 strands/inch, a weft density was 142 strands/inch, a cover factor CF was 1917, a thickness was 100 μm, permeability was 1573 mL/min/cm$^2$, and burst strength was 129 N. Further, an adaptation sheath diameter in a state in which the comparative graft base 5 is provided with a stent was 11 Fr. Seam slippage property was not determined, but there was no enlargement of needle hole formed by sewing of the base.

[Performance Evaluation of Body Lumen Graft Base]

The graft bases (the body lumen graft bases) 1 to 3 and the comparative graft bases 1 to 5 that have been obtained from the Examples and Comparative Examples were subjected to the following evaluation. The results are shown in the following Table 1.

<Intrinsic Viscosity>

An intrinsic viscosity was measured at concentration of 1.2 g/100 ml at 35° C. by using orthocholrophenol as a solvent.

<Weight Average Molecular Weight>

A weight average molecular weight was measured by gel permeation chromatography (GPC) using a GPC device under the following conditions using polymethyl methacrylate as a standard.

[Chemical Formula 2]
Device: Semimicro GPC System LC-20AD (manufactured by Shimadzu Corporation)
Detector: Shodex RI-104 (manufactured by Showa Denko K.K.)
Column: Shodex GPC LF-404 (manufactured by Showa Denko K.K.)
Column temperature: 40° C.
Solvent for mobile phase: 5 mmol/L $CF_3COONa$/1,1,1,3,3,3-hexafluoro-2-propanol (HFIP)
Flow rate: 0.45 ml/min
Injection amount: 20 μl
Sample preparation: To about 3 mg of a sample for measurement (polymeric material), 3 mL of flow rate indicator solution (mobile phase solvent containing 1% ethyl acetate) is added, dissolved under heating, and filtered through a 0.45 μm PTFE membrane filter.

<Thickness Measurement>

A whole thickness in the longitudinal direction of each graft base was measured by using a thickness gauge.

<Permeability>

Permeability of a graft base is measured according to ISO7198. Specifically, each graft base is cut to a size of about 2 cm×2 cm, to prepare a sample. Then, the sample is applied and set in the sample loading part (hole) 11 of the permeability measurement device 10 shown in FIG. 1. Water 12 is poured into the device while monitoring a water pressure using the pressure gauge 13, and an amount of water leaked through the sample for 1 minute at water pressure of 120 mmHg is measured and expressed as permeability (mL/min/cm$^2$).

<Adaptation Sheath Size (Adaptation Sheath Diameter)>

Figure 2B:
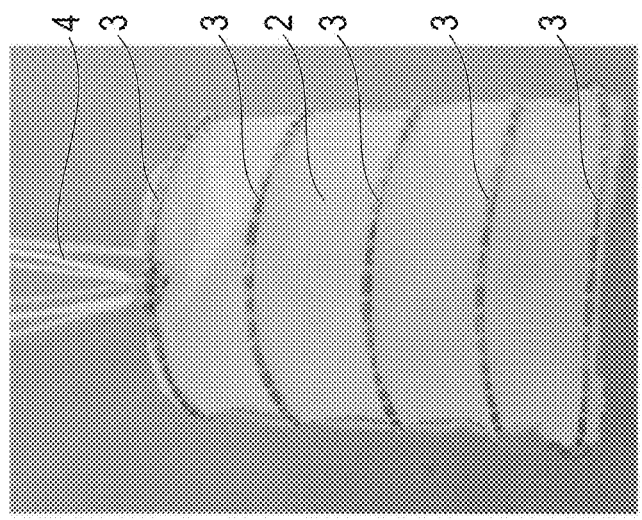
Figure 2A:
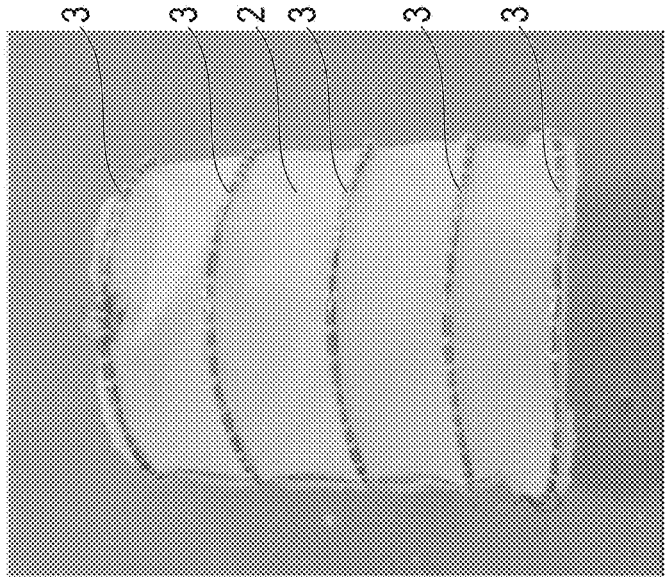

An adaptation sheath size of a graft base is measured according to the following method. Specifically, as shown in FIG. 2A, each graft base is sewn to each other in tublar shape (diameter of 26 mm, and length of 32 mm), to produce a graft 2. Then, five ring-shaped nickel-titanium stents 3 with φ28 mm are sewn to the graft 2 at an interval of 8 mm. Further, threads 4 for sliding inside a tube are attached to the end of the tublar base (FIG. 2B). Then, the base is inserted into a PTFE tube (sheath) 6 of various diameters using a SUS wire 5 with a diameter of 1.5 mm as a shaft, to measure a sliding force. The lowest diameter of PTFE tube (sheath) when the sliding force reaches 40 N or less is determined, to be regarded as an adaptation sheath size. Meanwhile, in the present test, for the sliding force, a load is measured by setting a PTFE tube (sheath) in an elongation tester and pulling a graft base using the threads at a rate of 200 mm/min in the PTFE tube. An average load applied for 3 to 5 seconds after starting to pull is calculated, to be regarded as a sliding force (N).

<Burst Strength>

Figure 3:
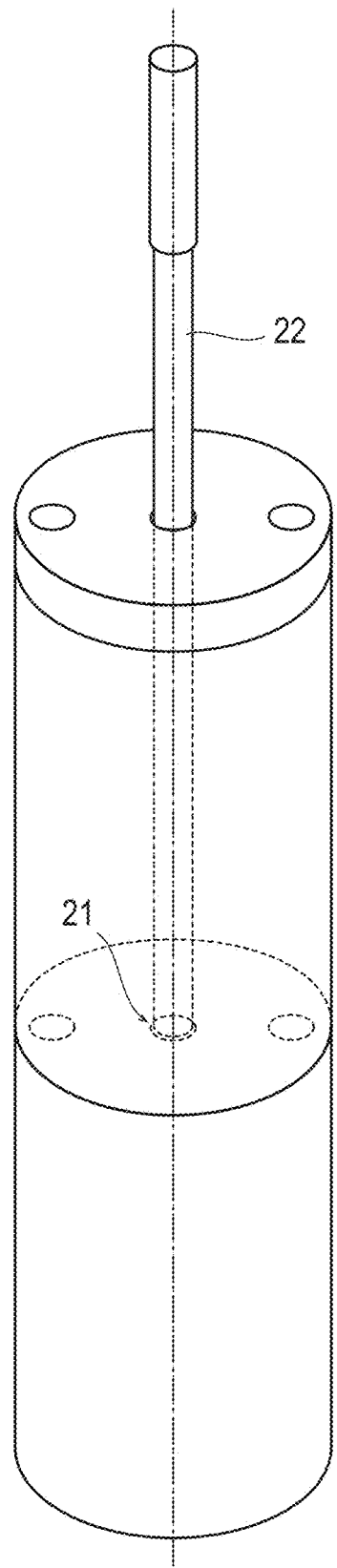
FIG. 3 is a diagram illustrating the measurement of burst strength.

Burst strength of a graft base is measured according to ISO7198. Specifically, each graft base is cut to a size of about 3 cm×3 cm, to prepare a sample. Then, as illustrated in FIG. 3, each graft base (sample) is applied and set in the sample loading part (hole) 21 with a diameter of 11.3 mm of the measurement device 20. Further, a press with globular tip (diameter of 11.3 mm) 22 is pushed into the sample at a speed of 125 mm/min, and a load (N) when the graft base is broken is measured, to be regarded as burst strength.

<Seam Slippage Property>

Figure 4A:
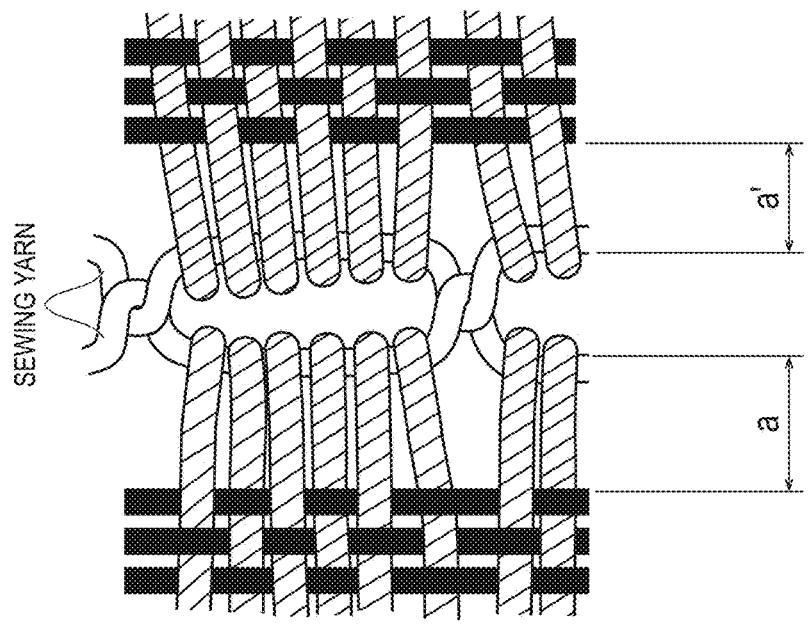
FIGS. 4A and 4B are diagrams illustrating the evaluation of enlarged needle hole formed by sewing.

Seam slippage property is measured according to JIS L1096 8.23.1b) (seam slippage method B) (2010). Specifically, five pieces of a test specimen (10 cm×17 cm) are obtained from each graft base, both in the width direction and height direction. Then, the test specimen is folded such that the surface can face the inside to have half of the original length. Then, it is cut along the folded line, and parts 1 cm apart from the end of the cut are sewn to each other under the following conditions as shown in FIG. 4A.

(Conditions for Face-to-Face Sewing))
Seam type: seam type is lock stitch;
Seam number: seam number is 5 eyes/cm; and
Type of sewing needle: sewing needle is common needle #11.

Figure 4B:
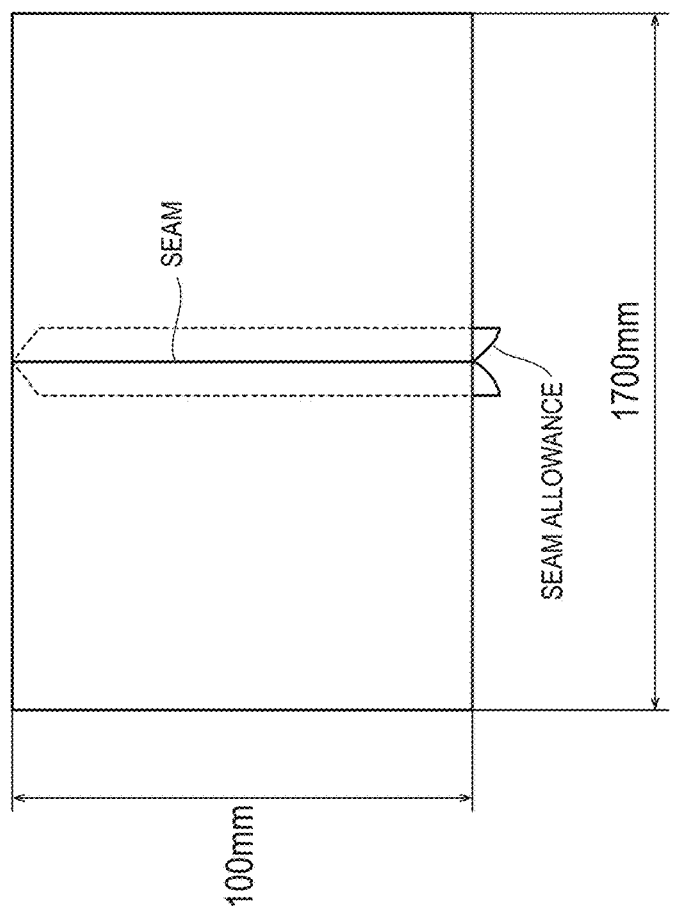

By using an elongation tester, a load of 49.0 N (5 kgf) is applied at an elongation rate of 30 cm/min with a grab space of 7.62 cm by a grab method. After removing the attached test specimen and keeping it for 1 hour, a load (about 20 N) allowing no loose part to be present near the seam is applied to the seam in the perpendicular direction to the seam, to measure a maximum hole size with seam slippage up to a unit of 0.1 mm. Here, a size of seam slippage is represented as "a+a' (mm)" as shown in FIG. 4B. An average value of five measurements both in the height direction and the width direction is calculated, and rounded to one decimal place. The expression "slippage in height direction" means slippage of a weft on a warp, and the expression "slippage in the width direction" means slippage of a warp on a weft.

<Enlarged Needle Hole>

According to the following method, enlarged needle hole is determined. Specifically, according to the method described in the above method for measuring adaptation sheath size, a graft 2 is prepared. Next, threads 4 for sliding inside the tube are attached to the end of the tublar base (FIG. 2B). Then, the base is inserted into a PTFE tube (sheath) having an inner diameter of adaptation sheath size using a SUS wire 5 with a diameter of 1.5 mm as a shaft. Thereafter, the graft 2 is pulled out of the PTFE tube using the threads 4, to observe from the inner side of the graft 2 by using a magnifier, or the like whether seam provided with the stent 3 by sewing is enlarged or not.

<Lowered Strength Caused by Hydrolysis>
(Conditions for Hydrolysis)

Six pieces of a graft base of Example 2, Example 3, or Comparative Example 1 are prepared in which each piece has been cut to a size of about 6 cm×12 cm. The cut graft base is added to a sealing vessel and completely immersed in a sufficient amount of phosphate buffered saline, and then kept in an oven at 90° C. After the keeping, one piece of each base is taken out on 7 days, 14 days, 21 days, 28 days, 35 days, or 42 days. It is washed with water and dried at room temperature.

(Change in Burst Strength)

From each base after the hydrolysis, a sample cut to a size of about 3 cm×3 cm is prepared. It is measured for burst strength according to the method for measuring burst strength. The burst strength of a sample without undergoing the hydrolysis is set as an initial value (after 0 day), and a graph is established by plotting the burst strength for the vertical axis and the number of days for hydrolysis at 90° C. for the horizontal axis. The results are shown in the following Table 2 and FIG. 6.

TABLE 2

| | Days for keeping in PBS at 90° C. | | | | | | |
|---|---|---|---|---|---|---|---|
| | 0 | 7 | 14 | 21 | 28 | 35 | 42 |
| Example 2 | 157 | 145 | 125 | 100 | 72 | 47 | 31 |
| Example 3 | 180 | 175 | 162 | 145 | 125 | 100 | 70 |
| Comparative Example 1 | 176 | 168 | 155 | 140 | 122 | 97 | 76 |

Figure 5A:
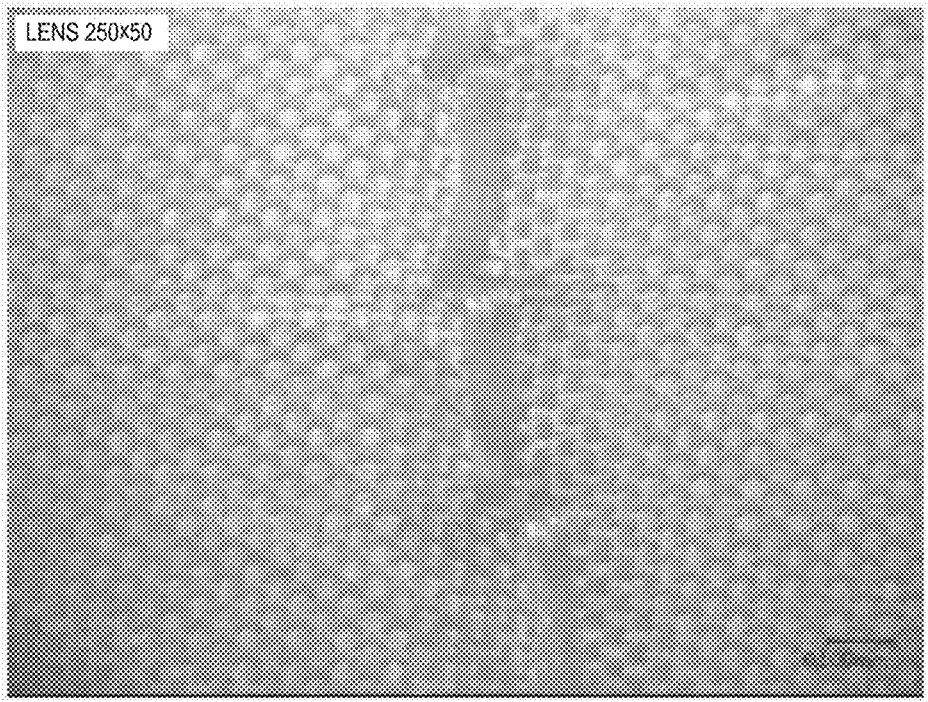
FIGS. 5A and 5B are enlarged photographic images of a base surface after the evaluation of enlarged needle hole formed by sewing of the graft base 3 of Example 3 (FIG. 5A) and the comparative graft base 4 of Comparative Example 4 (FIG. 5B).
Figure 5B:
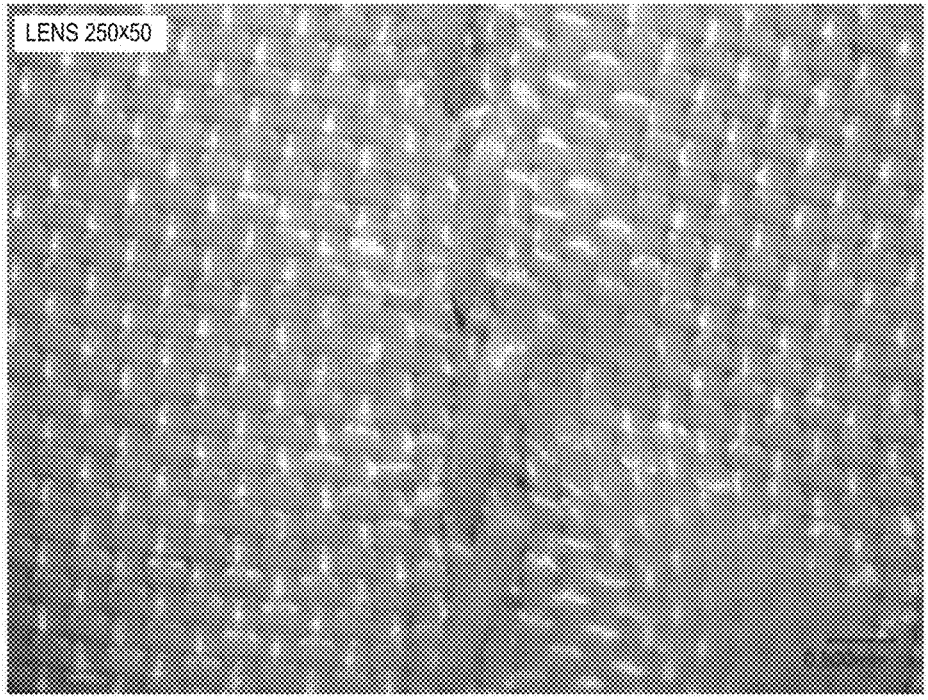

It is noted from the Table 1 and FIGS. 5A and 5B that the graft bases 1 to 3 of the present invention have both low permeability and high strength (burst strength), although they have a thin thickness. It is also shown that the graft bases 1 to 3 of the present invention can be inserted to a catheter of 11 Fr, and that decreased diameter by 2 Fr as compared to Comparative Example 1 (conventional base) or Comparative Example 2 (base obtained by calender treatment of a conventional base) can be achieved for the stent graft system. The seam slippage property of the graft base 1 of the present invention is 1.4 mm in the height direction and 0.8 mm in the width direction, to be found that the average value of the height direction and the width direction is 1.2 mm. The seam slippage property of the graft base 2 is 1.2 mm in the height direction and 1.0 mm in the width direction, to be found that the average value of the height direction and the width direction is 1.1 mm. The seam slippage property of the graft base 3 was 1.0 mm both in the height direction and the width direction. Enlarged needle hole is not observed in any base. In particular, the graft base 3 of the present invention exhibits burst strength of 180 N, which is higher than that of the graft base 2 of Example 2 using the same fibers. It is observed that the improved burst strength can be achieved by increased intrinsic viscosity of PET (increased molecular weight of PET).

On the other hand, the comparative graft base 1 has high strength but can be inserted to a catheter with 13 Fr or more. Further, the comparative graft base 2 has a smaller thickness, but the adaptation sheath diameter after being provided with a stent is large as of 13 Fr, because it is formed of multifilament of thick filaments (a single fiber fineness of 1.6

TABLE 1

| Sample | | | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|---|
| Total | Warp | (dtex) | 39 | 39 | 39 | 44 | 44 | 56 | 44 | 39 |
| fineness | Weft | (dtex) | 39 | 39 | 39 | 44 | 44 | 84 | 44 | 39 |
| Single | Warp | (dtex) | 0.043 | 0.0047 | 0.0047 | 1.6 | 1.6 | 2.0 | 2.2 | 0.0047 |
| fiber fineness | Weft | (dtex) | 0.043 | 0.0047 | 0.0047 | 1.6 | 1.6 | 2.0 | 2.2 | 0.0047 |
| Yarn | Warp | (strands/inch) | 183 | 177 | 185 | 163 | 163 | 112 | 129 | 165 |
| density | Weft | (strands/inch) | 129 | 128 | 133 | 124 | 124 | 84 | 119 | 142 |
| Cover factor | | | 1948 | 1905 | 1986 | 1904 | 1904 | 1608 | 1645 | 1917 |
| Weight average molecular weight (interms of polymethyl methacrylate: Mw) | | | 14,500 | 14,500 | 24,700 | 14,900 | 14,900 | 15,000 | 25,000 | 14,500 |
| Intrinsic viscosity (IV) | | | 0.6 | 0.6 | 1.0 | 0.6 | 0.6 | 0.6 | 1.0 | 0.6 |
| Press treatment | | | Yes | Yes | Yes | No | Yes | Yes | Yes | No |
| Thickness | (μm) | | 68 | 65 | 69 | 120 | 80 | 62 | 72 | 100 |
| Permeability (ISO7198) | (mL/min/cm$^2$) | | 57 | 168 | 128 | 200 | 49 | 20 | 371 | 1,573 |
| Burst strength (ISO7198) | (N) | | 178 | 157 | 180 | 176 | 176 | 149 | 153 | 129 |
| Seam slippage property (JISL1096) | Height direction (mm) | | 1.4 | 1.2 | 1.0 | NA | NA | 1.9 | 1.4 | NA |
| | Width direction (mm) | | 0.8 | 1.0 | 1.0 | NA | NA | 2.0 | 1.7 | NA |
| Adaptation sheath diameter | (Fr.) | | 11 | 11 | 11 | 13 | 13 | 11 | 1.1 | 11 | dtex) without any change in cover factor (amount of thread per unit area). Further, the comparative graft base 3 has a lower cover factor (woven at a low density) so that the adaptation sheath diameter can be as small as 11 Fr, while the strength (burst strength and thread maintaining strength) is lowered. Furthermore, the seam slippage property is so high as of 1.9 mm in the height direction and 2.0 mm in the width direction, and enlarged hole size in the seam is observed, demonstrating that blood leakage (type IV end leak) would be induced. Like Comparative Example 3, the comparative graft base 4 has a small cover factor so that the adaptation sheath diameter can be as low as 11 Fr when it is provided with a stent. Further, due to increased molecular weight (increased intrinsic viscosity) of the thread material (PET), the strength (burst strength and thread maintaining strength) can be improved, while the seam slippage property is so high as of 1.4 mm in the height direction and 1.7 mm in the width direction, to be found that the average value of the height direction and the width direction is 1.6 mm, and enlarged hole size in the seam is observed, demonstrating that blood leakage (type IV end leak) would be induced. The comparative graft base 5 is the same fabric as the graft base 2, but without having the calender treatment, the permeability is 1573 mL/min/cm$^2$, demonstrating that blood leakage (type IV end leak) would be induced.

The graft base 2 of the present invention is formed of polyethylene terephthalate having almost the same weight average molecular weight and also almost the same cover factor (almost the same intrinsic viscosity) as the comparative graft base 1. However, as it is formed of thin filaments (a single fiber fineness of the graft base 2 of the present invention is 0.0047 dtex while a single fiber fineness of the comparative graft base 1 is 1.6 dtex), the strength (burst strength) is lower and, as it is shown in FIG. 6, decrease in strength (decrease in burst strength) caused by hydrolysis is observed faster than that of the comparative graft base 1. However, the graft base formed of polyethylene terephthalate with higher molecular weight (higher intrinsic viscosity) like the graft base 3 of the present invention shows high strength (burst strength) and decrease in strength (decrease in burst strength) caused by hydrolysis is observed at the same level as the comparative graft base 1 having a thick filament, and thus it is observed that the resistance to hydrolysis can be improved.

The present application is based on Japanese Patent Application No. 2013-144259 filed on Jul. 10, 2013, and the disclosure thereof is herein incorporated by reference in its entirety.

The invention claimed is:

1. A body lumen graft base having at least one surface of a woven fabric comprising a fiber having a total fineness of 1 to 80 decitex and a single fiber fineness of less than 0.1 decitex subjected to press treatment, wherein a yarn density of weft of the fiber is 133 strands/inch or less.

2. The body lumen graft base according to claim 1, wherein the press treatment is press treatment by a calender machine.

3. The body lumen graft base according to claim 1, wherein a cover factor is 1400 to 3000.

4. The body lumen graft base according to claim 1, wherein the woven fabric is formed by a polyester fiber having a weight average molecular weight of 10,000 to 50,000.

5. The body lumen graft base according to claim 1, wherein the woven fabric has a thickness of 1 to 90 μm.

6. The body lumen graft base according to claim 1, wherein the fiber having the total fineness is a multifilament of 100 or more of single filaments.

7. A method for producing a body lumen graft base, the method comprising producing a woven fabric from fibers having a total fineness of 1 to 80 decitex and a single fiber fineness of less than 0.1 decitex, and subjecting at least one surface of the woven fabric to calender treatment, wherein a yarn density of weft of the fiber is 133 strands/inch or less.

8. A body lumen graft comprising the body lumen graft base set forth in claim 1, and a stent.

9. The body lumen graft base according to claim 2, wherein a cover factor is 1400 to 3000.

10. A body lumen graft comprising a body lumen graft base produced by the method set forth in claim 7, and a stent.

11. The body lumen graft base according to claim 1, wherein a yarn density of weft of the fiber is at least 128 strands/inch and at most 133 strands/inch.

12. The method according to claim 7, wherein a yarn density of weft of the fiber is at least 128 strands/inch and at most 133 strands/inch.

13. A body lumen graft comprising a body lumen graft base produced by the method set forth in claim 12, and a stent.

\* \* \* \* \*